US011509630B2

(12) United States Patent
Salin et al.

(10) Patent No.: US 11,509,630 B2
(45) Date of Patent: Nov. 22, 2022

(54) INTERFACE PROXY DEVICE FOR CYBER SECURITY

(71) Applicant: Roche Diagnostics Operations, Inc., Indianapolis, IN (US)

(72) Inventors: Richard Edward Salin, Zug (CH); Alejandro Morcillo Montejo, Girona (ES)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 102 days.

(21) Appl. No.: 16/876,595

(22) Filed: May 18, 2020

(65) Prior Publication Data
US 2020/0382472 A1    Dec. 3, 2020

(30) Foreign Application Priority Data

May 29, 2019  (EP) .................................... 19177438

(51) Int. Cl.
| | | |
|---|---|---|
| *G06F 15/177* | (2006.01) | |
| *H04L 9/40* | (2022.01) | |
| *G06F 21/57* | (2013.01) | |
| *H04L 67/12* | (2022.01) | |
| *H04L 67/00* | (2022.01) | |
| *H04L 67/5682* | (2022.01) | |

(52) U.S. Cl.
CPC .......... *H04L 63/0281* (2013.01); *G06F 21/57* (2013.01); *H04L 63/1408* (2013.01); *H04L 67/12* (2013.01); *H04L 67/34* (2013.01); *H04L 67/5682* (2022.05)

(58) Field of Classification Search
None
See application file for complete search history.

(56) References Cited

U.S. PATENT DOCUMENTS 7,464,407 B2   12/2008  Nakae et al.
8,307,215 B2   11/2012  Camiel
(Continued)

FOREIGN PATENT DOCUMENTS

EP       1168165 A2   1/2002
EP       1505499 A1   2/2005
(Continued)

*Primary Examiner* — Phuoc H Nguyen
(74) *Attorney, Agent, or Firm* — Roche Diagnostics Operations, Inc.

(57) ABSTRACT

A system for providing cyber protection to medical devices in a medical environment is presented. The system comprises a medical device comprising software services, a backend server to maintain and provide software updates to medical devices, and an interface proxy box connected to the medical device and in communication with the backend server. The interface proxy box determines the software services resident on the medical device. The interface proxy box installs the software services determined to be resident on the medical device on the interface proxy box and configures the installed software services to match the software services resident on the medical device. The interface proxy box communicates periodically with the backend server and receives and applies security updates to the software services installed and configured on the interface proxy box. The medical device utilizes the updated software services on the interface proxy box.

14 Claims, 3 Drawing Sheets

(56) References Cited

U.S. PATENT DOCUMENTS

| | | | |
|---|---|---|---|
| 9,485,218 B2 | 11/2016 | Harp et al. | |
| 10,990,376 B2* | 4/2021 | Gandhi | H04L 67/025 |
| 2008/0301798 A1 | 12/2008 | Hao et al. | |
| 2013/0036412 A1 | 2/2013 | Birtwhistle et al. | |
| 2015/0040231 A1 | 2/2015 | Oliphant et al. | |
| 2017/0039372 A1* | 2/2017 | Koval | G01R 22/06 |
| 2017/0134474 A1* | 5/2017 | Gao | H04L 67/125 |
| 2018/0060105 A1 | 3/2018 | Shimizu | |
| 2019/0102533 A1* | 4/2019 | Sagar | G06F 21/34 |
| 2019/0373472 A1* | 12/2019 | Smith | H04L 9/3239 |
| 2020/0257797 A1* | 8/2020 | Monson | G06F 21/552 |

FOREIGN PATENT DOCUMENTS

| | | |
|---|---|---|
| JP | 1091453 A | 4/1998 |
| JP | 2017-078899 A | 4/2017 |
| WO | 2016/193831 A1 | 12/2016 |

* cited by examiner

INTERFACE PROXY DEVICE FOR CYBER SECURITY

CROSS-REFERENCE TO RELATED APPLICATIONS

This application claims priority to EP 19177438.9, filed May 29, 2019, which is hereby incorporated by reference.

BACKGROUND

The present disclosure generally relates to cybersecurity for medical devices and, in particular, to deploying rapid cybersecurity updates for medical devices.

The medical devices typically face strict and continuous requirements regarding the cybersecurity of the devices. For example, the US Food and Drug Administration (FDA) is currently drafting recommendations stating that any found cyber vulnerability shall be addressed and fixed within thirty days of discovery of the cyber vulnerability with no interference regarding the performance of the medical device. As the medical devices tend to acquire more and more cyber interfaces as well as a growing number of Off the Shelf Software (OTSS) components, all capable of introducing vulnerabilities to the medical device, responding in a timely matter can be a huge challenge.

Currently, if a vulnerability is discovered such as, for example, WannaCry, every sector of a company along with the company's cybersecurity department needs to determine if any sectors have been affected and, if so, define an approach on how to address the issue at hand. This is very costly, e.g., a significant amount such as one million CHF for one such cyber vulnerability patch, and a slow, normal cyber vulnerability patch cycle can take approximately 6-12 months, thus not complying with the thirty-day timeline set by the FDA. One of the most severe issues can relate to vulnerabilities in libraries of exposed remote services. Fixing these service issues can require a patch for the infected library, which is typically part of the medical device software, thus triggering a complete software release. By segregating/mirroring these services into a separate interface proxy box, shared by all company medical devices, the vulnerable library can be patched in the separate interface proxy box once for all medical devices without triggering individual software updates. Leaving the vulnerable library on the medical device can be acceptable because this library is behind the patched and secure proposed separate interface proxy box.

Therefore, there is a need to explicitly monitor all interfaces of a medical device to create a unified cyber security solution over a common interface that is easily updated and/or patched in order to improve cyber security for that medical device.

SUMMARY

According to the present disclosure, a system for providing cyber protection to medical devices in a medical environment is presented. The system can comprise a medical device comprising a plurality of software services, a backend server configured to maintain and provide software updates to medical devices, and an interface proxy box connected to the medical device and in communication with the backend server. The interface proxy box can be configured to determine the plurality of software services resident on the medical device. The interface proxy box can be configured to install software libraries associated with the plurality of software services determined to be resident on the medical device on the interface proxy box and to configure the installed software libraries to match the plurality of software services resident on the medical device. The interface proxy box can be configured to communicate periodically with the backend server and to receive and apply security updates to plurality of software libraries installed and configured on the interface proxy box. The medical device can be configured to utilize the updated software libraries on the interface proxy box.

Accordingly, it is a feature of the embodiments of the present disclosure to explicitly monitor all interfaces of a medical device to create a unified cyber security solution over a common interface that is easily updated and/or patched in order to improve cyber security for that medical device. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

Certain terms will be used in this patent application, the formulation of which should not be interpreted to be limited by the specific term chosen, but as to relate to the general concept behind the specific term.

As used in the following, the terms "have", "comprise" or "include" or any arbitrary grammatical variations thereof can be used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, it can be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once.

The term 'medical device' as used herein can encompass any apparatus or apparatus component operable to execute one or more processing steps/workflow steps on one or more medical apparatus or system. The expression 'processing steps' thereby can refer to physically executed processing steps such as centrifugation, pipetting, aliquotation, reagent preparation, quality control QC preparation, sequencing library preparation, incubation, sample analysis and also sample transportation and the like.

The term 'communication network' as used herein can encompass any type of wireless network, such as a WIFI, GSM, UMTS or other wireless digital network or a cable based network, such as Ethernet or the like. For example, the communication network can comprise a combination of wired and wireless networks. In embodiments wherein units of the system can be comprised within one medical device, the communication network comprises communication channels within a medical device.

The present invention relates to a system for providing cyber protection to medical devices in a medical environment. The system can comprise a medical device comprising a plurality of software services, a backend server configured to maintain and provide software updates to medical devices, and an interface proxy box connected to the medical device and in communication with the backend server. The interface proxy box can be configured to determine the plurality of software services resident on the medical device. The interface proxy box can be configured to install the plurality of software services determined to be resident on the medical device on the interface proxy box and to configure the installed software services to match the plurality of software services resident on the medical device. The interface proxy box can be configured to communicate periodically with the backend server and to receive and apply security updates to plurality of software services installed and configured on the interface proxy box. The medical device can be configured to utilize the updated software services on the interface proxy box.

The present disclosure can provide an inventive technical solution to address the need to have a rapid response to medical device security concerns and vulnerabilities as required by the FDA. The interface proxy box can represent a security measure in which the interface proxy box can provide a level of cyber security to the underlying medical device. The present disclosure can provide an automated medical device specific setup, that is, the specific software services of the medical device can be mirrored and installed on the interface proxy box and on which the libraries and packages on the interface proxy box can be rapidly updated to ensure a minimal, thus hardened installation, on the interface proxy box.

The interface proxy box can comprise a medical device interface configured to communicate with a medical device. The interface proxy box can communicate with the medical device wirelessly or by a wired connection. The interface proxy box can be configured to have software services installed and configured on the interface proxy box that match, or mirror, the software services resident on the connected medical device. The interface proxy box can also comprise a backend server interface configured to communicate regularly with a backend server. The backend server can communicate with the interface proxy box via the backend server interface software services to update the libraries and packages of the software services installed on the interface proxy box. The interface proxy box can be configured to apply the software services library and package updates to the software services installed and configured on the interface proxy box. The connected medical device can then utilize the updated software services installed on the interface proxy box.

Security vulnerabilities typically can enter medical device systems via a connected interface such as, for example a networked interface, USB, serial, Bluetooth, WiFi, and the like. With this present disclosure, these interfaces can be fed into the interface proxy box instead of directly into the medical device. In one embodiment, the interface proxy box can be configured to be placed internally within the medical device itself.

In another embodiment, the interface proxy box can be situated external to the medical device and can communicate over communication network such as, for example, an Ethernet connection, with the medical device. Alternatively, the interface proxy box can communicate with the medical device via a wired connection. Thus, the interface proxy box, in turn, can have a separate defined interface to the medical device. These multiple interfaces that are fed into the interface proxy box can, then, be monitored and the interface drivers can be easily patched on the interface proxy box without interacting with the medical device at all, thereby, avoiding the need for any revalidation of the medical device due to software updates and patches.

This way the SSL libraries can be patched and updated on the interface proxy box without having to patch, or update, the software services on the actual medical device itself. Additionally, USB mass storage devices can provide their content as a server message block (SMB) shares and all security concerns and vulnerabilities can be addressed via this interface proxy box without involving the medical device.

In one embodiment, an input device can be connected directly to the interface proxy box. The interface proxy box can be configured to analyze any input signals coming from the input device before that input is sent to the medical device. The input device can be, for example, a barcode scanner, RFID receiver, keyboard, touch screen, or combinations thereof. These inputs can be checked for known SQL injection (or any other harmful injection) command by analyzing the input at the interface proxy box, thereby, providing another layer of cyber security for the medical device.

Further, additional monitoring modules can be developed for the interface proxy box, thereby, removing these monitoring efforts from the medical device itself. Thus, the interface proxy box can be shared amongst several medical devices, which may rely on this one input accessory.

In an additional embodiment, a virus scanner can also be added to the interface proxy box and a common firewall can also be implemented along with packet inspection to address any specific targeted cyber-attacks directed towards the interface proxy box before the cyber-attacks can reach the medical device.

In another embodiment, support for a whole range of additional modules can also be built into the interface proxy box to allow for security features to easily be expanded over time along with support to integrate cloud-based remote services such as, for example, for the purpose of remote services activities.

Because different medical devices rely on different software services, the interface proxy box needs to adapt accordingly. This can be achieved by the initial interface proxy box being a generic, bare bones version that detects the underlying software services of the medical device to be protected only after the interface proxy box is initially connected to the medical device. After the initial connection with the medical device and determination of the medical device's software services, the interface proxy box can request from a controlled backend server only those particular libraries and packages associated with the specific software services setup of that particular medical device. This can result in a repository of trusted software services to be setup on the connected interface proxy box and can provide a supported set of mirrorable software services that can be automatically configured according the configuration of the underlying medical device host.

The interface proxy box can be a physical piece of hardware directly connected (for example, internally) to the medical device to be protected. This can be essential, as there can be a need to possibly update all the software (including the kernel and the like) on this interface proxy box. Because the software services on the medical device can remain somewhat vulnerable (but not exposed since the medical device only interface is connected directly to the interface proxy box), it can be essential that one cannot access the software services directly from the medical device but would always need to go through the interface proxy box.

By placing the hardware interface proxy box next to the medical system or medical device and using the interface proxy box to connect to a communication network such as, for example, LAN, WIFI or WAN, can allow the application of security and control mechanisms to be released faster using independent lifecycles from the medical device or system. The cyber security and control mechanisms can go from identifying the medical device or system properly, anonymizing configured data, encrypting the data and the transportation channel, compliance with new security constraints (regulations or internals from the customer), redirecting messages to different locations with the ability to simultaneously communicate to multiple channels in different protocols and for each channel different control criteria could be applied with a highly granular but centralized configuration.

This approach can be particularly advantageous for older legacy medical devices that cannot be updated or patched due to the operating system installed on the medical device and/or the inability to connect to a backend server because of outdated hardware issues.

This approach can reduce the cyber security effort per medical device as the interface proxy box can be reused, i.e., the interface proxy box can be moved from one medical device to another and can be reconfigured to mirror the new medical device. The interface proxy box can also allow a quick, easy, and affordable response to a majority of the cyber security issues. The interface proxy box can essentially create a border of defense around the interfaces securing the medical device itself and allowing the medical device's software updates to be postpone to the next "normal" software update while still maintaining a high level of security against day-to-day cyber security threats.

The isolated interface proxy box can also be used to enable certain security features in a medical device. For example:
 *Transmit results to printers—Possibility to transmit results and any other information to a printer protocol so that the medical device can be connected to a printer through the interface proxy box. If any new printer is added to the medical system environment or the customer needs to print more than one label of the same message, the interface proxy box can create multiple channels to the different printers and transmit the message accordingly.
 *Direct connection and transformation of message to integrate with EMR and Enterprise Solutions—Connecting medical devices and systems to other systems can require complex transformation of messages and integration overhead. Implementing these features in each and every medical device can be expensive and requires inclusion within the lifecycle of the medical device which can be long or difficult to change. The interface proxy box can allow the development of customized drivers that can interact with the medical device and the target system with the support of additional systems (if needed) so that this integration functionality can be implemented and handled independently of the medical device itself.
 *Integration with RFID reader to enable easy sign in processes in legacy devices—As regulations and hospital/lab infrastructure complexity change over time, new security needs may arise that still need to include all the functionality of each medical device which can be difficult or impossible if the manufacturer does not want to include that medical device in the lifecycle. If the medical device implements workflows or events for authenticating users, the interface proxy box can be used as an interface for supporting new features such authenticating users via RFID simplifying the process and improving in efficiency
 *Monitoring and analytics—The interface proxy box can extend the systems of the company by enabling monitoring and analytical features without modifying the system's internal behavior, enabling a medical device company to track the status of the medical devices (including, when available, business events) and systems that are in the field and advance the needs of the customers.

Separating security vulnerabilities coming from a connected interface into an isolated interface proxy box with a defined interface towards the main medical device can have several advantages. One such advantage is the interface proxy box can be patched and updated without interfering with or involving the main medical device.

Another important advantage can be that the interface proxy box can self-configure for many different medical devices and can only install the software needed for the medical device it is physically connected to.

Additionally, the interface proxy box can have the advantage that it can be reused or easily moved from one medical device to another.

Further, the interface proxy box can support a whole range of additional modules, wherein the support can be built into the interface proxy box allowing security features to easily be expanded over time. The interface proxy box can also support integrated remote services such as, for example, for the purpose of remote services activities.

In another alternative embodiment, the interface proxy box can be updated manually, for example, by exchanging the interface proxy box or installing the new features on the interface proxy box. This can provide the advantage that the interface proxy box can run without being connected to the backend server. However, using this embodiment, the timeframe for addressing security vulnerabilities may still remain too long for regulatory agencies and the medical device could stay vulnerable.

A computer implemented method for providing cyber protection to medical devices in a medical environment is also provided. The method can comprise connecting an interface proxy box to a medical device, connecting the interface proxy box to a backend server via a communication connection, obtaining by the interface proxy box details regarding the underlying software services resident on the medical device, requesting by the interface proxy box the underlying software services of the medical device from the backend server, receiving and installing the software services of the medical device from the backend server onto the interface proxy box, configuring and mapping the software services of the medical device on the interface proxy box such that the software services installed on the interface proxy mirror the software services associated with the underlying software services resident on the medical device, periodically synchronizing the interface proxy box with the backend server, receiving and applying updates and patches from the backend server for the software services of the medical device installed and configured on the interface proxy box when updates and patches are detected, and utilizing the updated medical device software services on the interface proxy box by the medical device.

The computer implemented method can further comprise analyzing input from an input device by the interface proxy box before the input is received by the medical device.

The computer implemented method can further comprise connecting the interface proxy box to the medical device via a wireless connection, such as, for example, an Ethernet connection. The interface proxy box can also be connected to the medical device via a direct connection, such as, for example, a USB connection.

In one embodiment, receiving and applying security updates to the libraries installed and configured on the interface proxy box from the backend server can be performed manually.

In one embodiment, the updates and patches can be security updates. These security updates can be installed and configured on the interface proxy box when such security vulnerabilities are detected.

In one embodiment, the receiving and applying updates and patches to the libraries installed and configured on the interface proxy box from the backend server can be performed manually.

In summary, the interface proxy box can allow a quick, easy and affordable response to a majority of the cyber security issues, thereby, creating a border of defense around the interfaces before such cyber security issues can possibly reach the connected medical device. In addition, any updates or patches to the software services resident on the interface proxy box may not depend on a software update or patch of the connected medical device.

Figure 1:
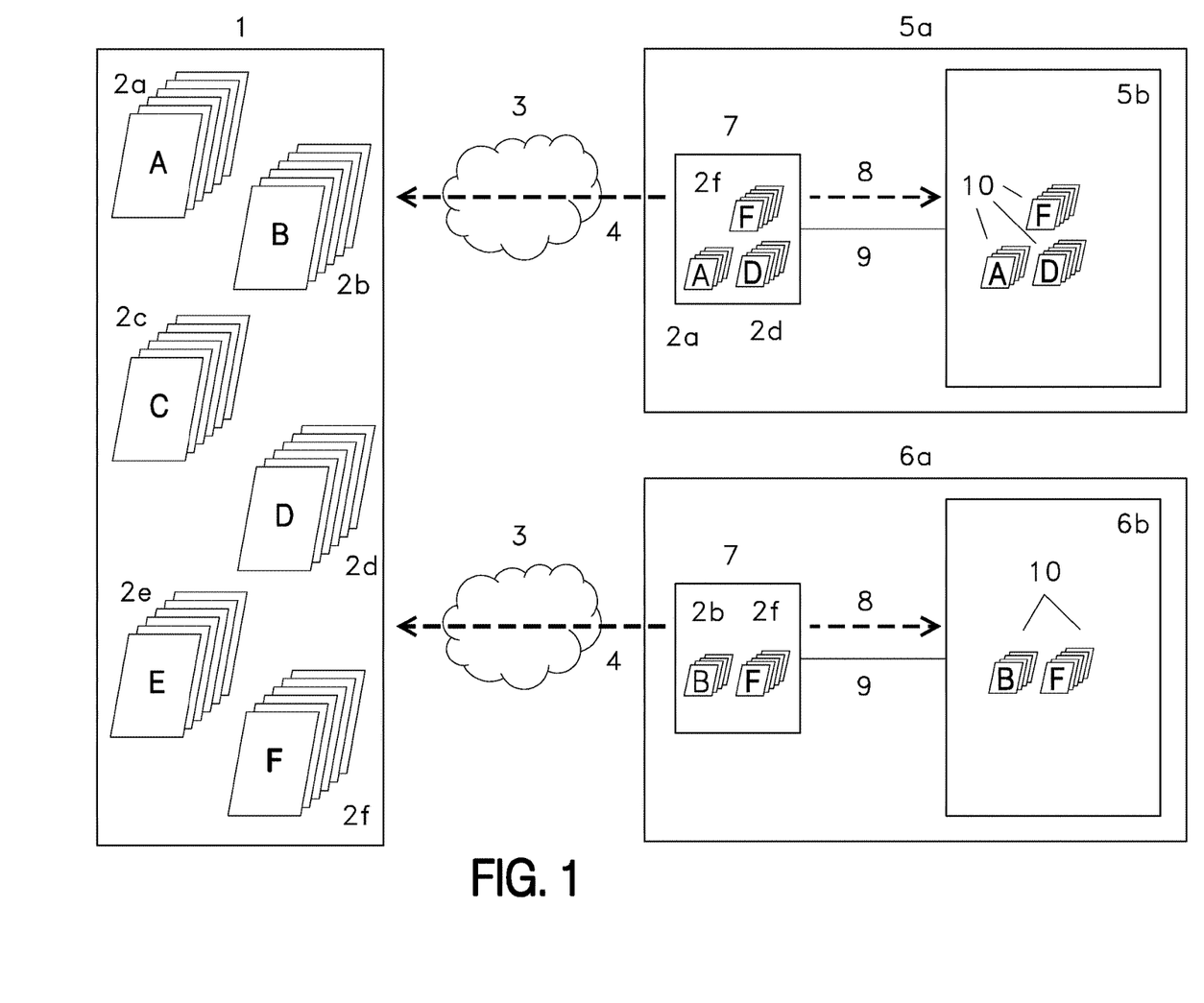
FIG. 1 illustrates the schematic set up of the box according to an embodiment of the present disclosure.

Referring initially to FIG. 1, FIG. 1 illustrates the schematic set up for the configuration process of an interface proxy box 7. Generally, the interface proxy box 7 can be a generic interface proxy box, i.e., the interface proxy box 7 does not have any software services installed on it. The interface proxy box 7 can be initially first connected directly to the medical device 5b, 6b via a communication network 9 such as, for example, an Ethernet connection within a medical system 5a, 5b. In another embodiment, the interface proxy box 7 can be integrated into and directly connected to the medical device 5b, 6b itself.

After the first connection 9 between the interface proxy box 7 and the medical device 5b, 6b is established, the interface proxy box 7 can communicate with the medical device 5b, 6b via the communication connection 9 and can determine the software services 10 resident on and used by the medical device 5b, 6b. For example, and as is illustrated in FIG. 1, in the first medical system 5a, the interface proxy box 7 can determine that the medical device 5b has the A, D, and F software services 10 installed on the medical device 5b and, in the second medical system 6a, the interface proxy box 7 can determine that the medical device 6b has the B and F software services 10 installed in the medical device 6b.

The interface proxy box 7 can then request from a backend server 1 (via another communication network such as, for example, the internet/cloud 3) the newest version of the software services 10 libraries 2a-f associated with those specific software services 10 resident on the particular medical device 5b, 6b. For example, and as is illustrated in FIG. 1, the interface proxy box 7 connected to the medical device 5b can request libraries 2a, 2d, and 2f from the backend server 1, whereas the interface proxy box 7 connected to the medical device 6b can request libraries 2b and 2f. Depending on the specific software services 10 resident on the medical device 5b, 6b, the interface proxy box 7 can install those specific software services 10 and can configure itself to match or mirror 8 the software services 10 resident on the particular medical device 5b, 6b that the interface proxy box 7 is connected to. Thereby, the interface proxy box 7 can customize itself to the particular medical device 5b, 6b to which it is connected. Therefore, due to the customization process during set-up of the interface proxy box 7, only one interface proxy box type 7 may be necessary for all types of medical devices 5b, 6b. Additionally, the interface proxy box 7 can be reusable and interchangeable between all types of medical devices.

The interface proxy box 7 can synchronize itself (again via a network connection such as, for example, the internet/cloud 3) with the backend server 1 on a regular/scheduled basis as is deemed necessary. If it is determined during synchronization that there is an update or patch required for any of the software services 10 installed on the medical devices 5b, 6b, the backend server 1 can provide the update and/or patch to the specific libraries 2a-f for those specific software services 10 of the medical devices 5b, 6b installed on interface proxy box 7. The medical device 5b, 6b, then, in turn, can use those updated and/or patched libraries 2a-f installed on the interface proxy box 7.

Figure 2:
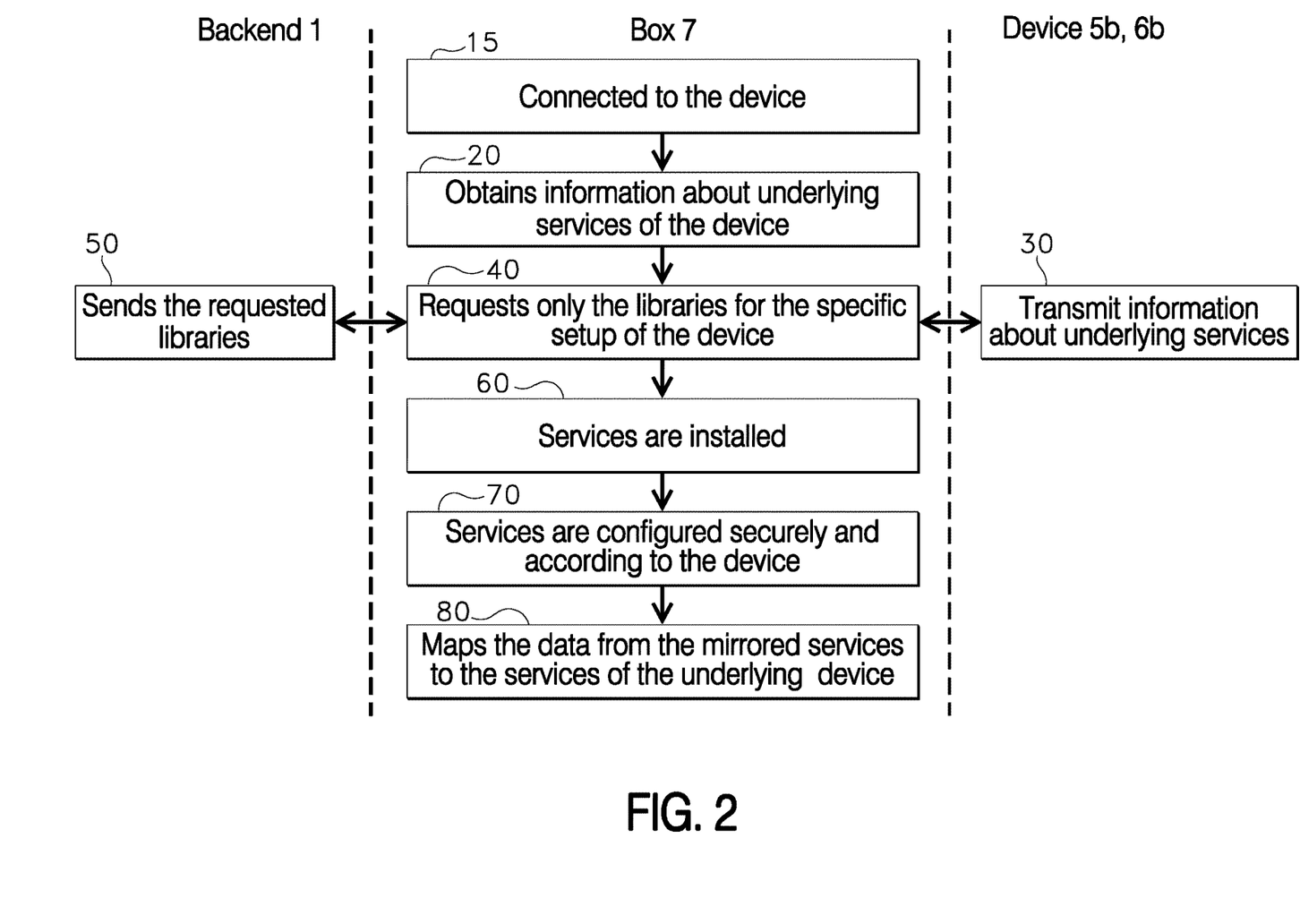
FIG. 2 illustrates the workflow for the configuration process of the interface proxy box according to an embodiment of the present disclosure.

Turning to FIG. 2, FIG. 2 illustrates the typical workflow for the initial configuration process of the interface proxy box 7 using a swim lane illustration of the backend server 1, the interface proxy box 7, and medical device 5b, 6b.

Starting with step 15, a new generic interface proxy box 7 can be connected to a medical device 5b, 6b via a communication connection such as, for example, an Ethernet connection 9 or a USB device. In step 20, the interface proxy box 7 can then request and obtain information regarding the specific underlying software services 10 resident on the medical device 5b, 6b via the communication connection such as, for example, an Ethernet connection 9 or USB device between the interface proxy box 7 and the medical device 5b, 6b. Turning to step 30, the medical device 5b, 6b in conjugation with the request from the interface proxy box 7 can transmit the information about specific underlying software services 10 of the medical device 5b, 6b via the communication connection such as, for example, an Ethernet connection 9 or a USB device as mentioned above.

Based on that software services 10 information received by the medical device 5b, 6b in step 30, the interface proxy box 7 can request, in step 40, via another communication connection such as, for example, the internet/cloud 3, from a backend server 1 only the necessary libraries 2a-f for the specific software services 10 setup of the connected medical device 5b, 6b. In step 50, the backend server 1 can send the requested software services 10 libraries 2a-f to the interface proxy box 7 via the other communication connection such as, for example, internet/cloud 3 in conjugation with the request from the interface proxy box 7.

In step 60, the requested software services 10 of the connected medical device 5b, 6b and the libraries 2a-f associated with those software services 10 of the connected medical device 5b, 6b received from the backend server 1 can be installed on the interface proxy box 7.

In step 70, the installed software services 10 received from the backend server 1 can be configured securely on the interface proxy box 7 according to the specific software services setup of the medical device 5b, 6b.

Finally, in step 80, the interface proxy box 7 can mirror, or map, 8 the data from the libraries 2a-f from the mirrored software services now configured and installed on the interface proxy box 7 to the specific software services 10 resident on the underlying connected medical device 5b, 6b.

Figure 3:
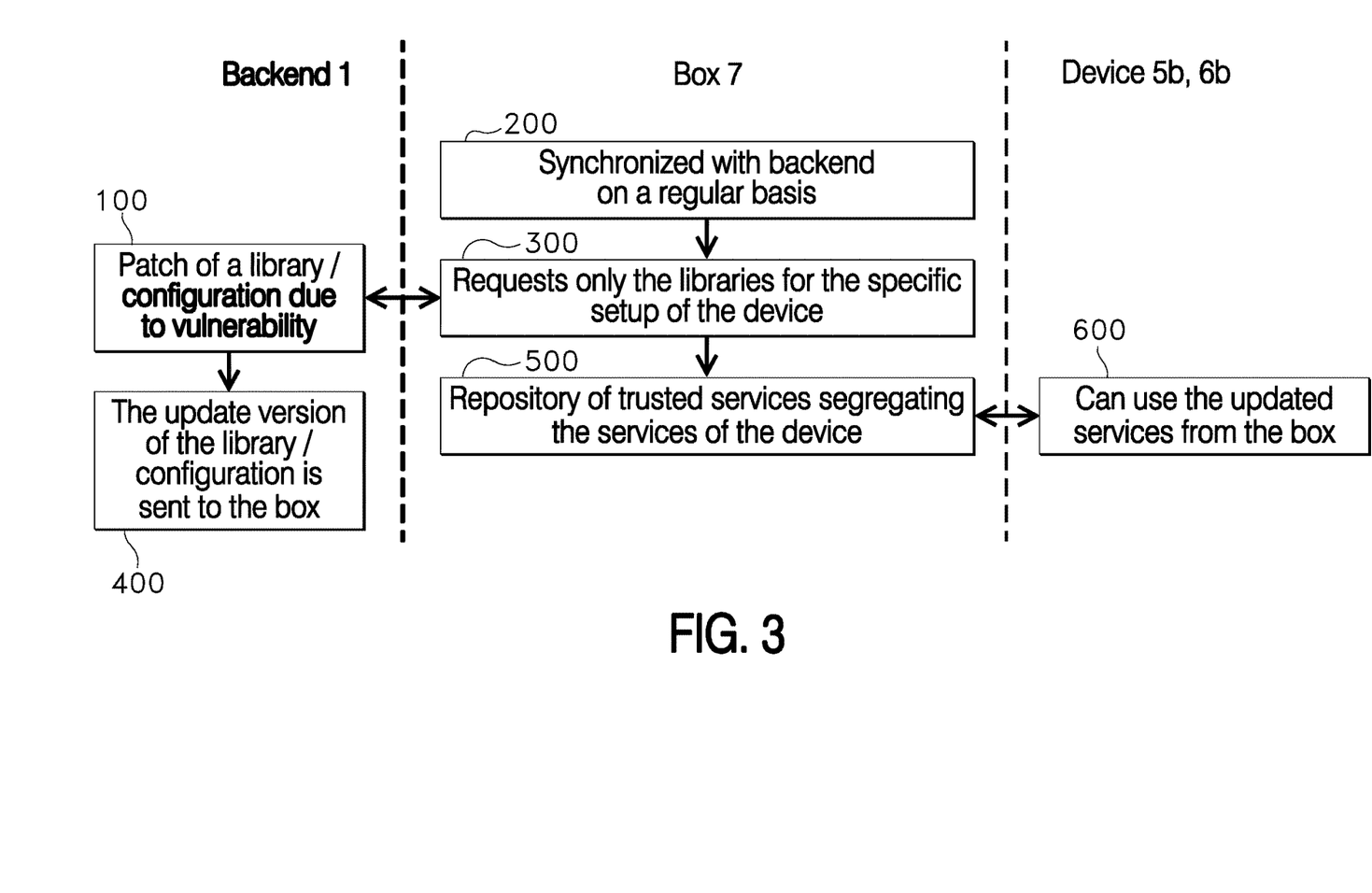
FIG. 3 illustrates the workflow for updating the interface proxy box according to an embodiment of the present disclosure.

Now, turning to FIG. 3, FIG. 3 illustrates the workflow for updating the interface proxy box 7 after the initial connection with, installation, and configuration of the medical device 5b, 6b via a communication connection 9 such as, for example, an Ethernet connection or USB device, using a swim lane illustration of the backend server 1, the interface proxy box 7, and medical device 5b, 6b.

In step 200, the interface proxy box 7 can synchronize/communicate with the backend server 1 on a regular basis via the other communication connection such as, for example, the internet/cloud 3. The synchronization/communication can be on a scheduled basis or can be when a new patch or update for the software services 10 of the connected medical device 5b, 6b is available or both.

In step 100, the backend server 1 can have a new patch and/or update for a library and/or configuration 2a-f for the software services 10 of the connected medical device 5b, 6b. In one embodiment, the new patch or update may be a newly discovered security vulnerability. Because the backend server 1 and the interface proxy box 7 synchronize/communicate on a regular basis via the other communication connection such as, for example, the internet/cloud 3, in step 400, the newly updated/patched version of the libraries/configuration 2a-f for the software services 10 of the connected medical device 5b, 6b can be sent to the interface proxy box 7 via the other communication connection such as, for example, the internet/cloud 3. Therefore, as soon as a library or configuration 2a-f update/patch software services 10 of the connected medical device 5b, 6b is created at the backend sever 1, the interface proxy box 7 can theoretically receive that updated version from the backend server 1.

In step 300, the interface proxy box 7 only requests from the backend server 1 the updated libraries/configurations 2a-f patches for the software services 10 of the connected medical device 5b, 6b that are necessary for the specific software services setup resident on the connected medical device 5b, 6b.

In step 500, the interface proxy box 7, therefore, can ensures that there is a repository of trusted software services that can be segregated from and protects the software services 10 resident on the connected medical devices 5b, 6b from potential cyber threats and attacks by providing an additional layer of protection.

Finally, in step 600, the medical device 5b, 6b can then use the updated software services 10 libraries 2a-f of the software services 10 of the connected medical device 5b, 6b installed and configured on the interface proxy box 7. This workflow can enable the medical device 5b, 6b to run the updated software services 10 on the interface proxy box 7 and, therefore, reduces the risk of cyber vulnerabilities in near real time.

Further disclosed and proposed is a computer program product including computer-executable instructions for performing the disclosed method in one or more of the embodiments enclosed herein when the program is executed on a computer or computer network. Specifically, the computer program may be stored on a computer-readable data carrier or a server computer. Thus, specifically, one, more than one or even all of method steps as indicated above may be performed by using a computer or a computer network, preferably by using a computer program.

As used herein, a computer program product refers to the program as a tradable product. The product may generally exist in any format, such as in a paper format, or on a computer-readable data carrier on premise or located at a remote location. Specifically, the computer program product may be distributed over a data network (such as a cloud environment). Furthermore, not only the computer program product, but also the execution hardware may be located on premise or in a cloud environment.

Further disclosed and proposed is a computer-readable medium comprising instructions which, when executed by a computer system, cause a laboratory system to perform the method according to one or more of the embodiments disclosed herein.

Further disclosed and proposed is a modulated data signal comprising instructions, which, when executed by a computer system, cause a laboratory system to perform the method according to one or more of the embodiments disclosed herein.

Referring to the computer-implemented aspects of the disclosed method, one or more of the method steps or even all of the method steps of the method according to one or more of the embodiments disclosed herein may be performed by using a computer or computer network. Thus, generally, any of the method steps including provision and/or manipulation of data may be performed by using a computer or computer network. Generally, these method steps may include any of the method steps, typically except for method steps requiring manual work, such as providing the samples and/or certain aspects of performing the actual measurements.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A system for providing cyber protection to medical devices in a medical environment, the system comprising:
a medical device comprising a plurality of software services;
a backend server configured to maintain and provide software updates to medical devices; and
an interface proxy box connected to the medical device and in communication with the backend server, wherein the interface proxy box is configured to determine the plurality of software services resident on the medical device, wherein the interface proxy box is configured to install software libraries associated with the plurality of software services determined to be resident on the medical device on the interface proxy box and to configure the installed software libraries to match the plurality of software services resident on the medical device, wherein the interface proxy box is configured to communicate periodically with the backend server and to receive and apply security updates to plurality of software libraries installed and configured on the interface proxy box, and wherein the medical device is configured to utilize the updated software libraries on the interface proxy box.

2. The system according to claim 1, wherein the interface proxy box is connected to the medical device internally.

3. The system according to claim 1, wherein the interface proxy box is connected to the medical device externally.

4. The system according to claim 3, wherein the interface proxy box is connected externally to the medical device via a wireless and/or wired connection.

5. The system according to claim 1, further comprises,
an input device connected to the interface proxy box, wherein the interface proxy box is configured to analyze input from the input device before the input is sent to the medical device.

6. The system according to claim 5, wherein the input device is a barcode scanner, RFID receiver, keyboard, touch screen, or combinations thereof.

7. The system according to claim 1, wherein the interface proxy box is reusable.

8. The system according to claim 1, wherein the software services comprise libraries specific to the medical device.

9. The system according to claim 1, wherein the interface proxy box comprises a virus scanner.

10. A computer implemented method for providing cyber protection to medical devices in a medical environment, the method comprising:
connecting an interface proxy box to a medical device;
connecting the interface proxy box to a backend server via a communication network;
obtaining by the interface proxy box details regarding the underlying software services resident on the medical device;
requesting by the interface proxy box the underlying software services libraries of the medical device from the backend server;
receiving and installing the software services libraries of the medical device from the backend server onto the interface proxy box;
configuring and mapping the software services libraries of the medical device on the interface proxy box such that the software services libraries installed on the interface proxy box mirror the software services associated with the underlying software services resident on the medical device;
periodically synchronizing the interface proxy box with the backend server;
receiving and applying updates from the backend server for the software services libraries of the medical device installed and configured on the interface proxy box when updates are detected; and
utilizing the updated software services libraries of the medical device on the interface proxy box by the medical device.

11. The computer implemented method according to claim 10, wherein the updates are security updates installed and configured on the interface proxy box when vulnerabilities are detected.

12. The computer implemented method according to claim 10, further comprises, connecting the interface proxy box to the medical device via a wireless and/or wired connection.

13. The computer implemented method according to claim 10, wherein the receiving and applying updates to the libraries installed and configured on the interface proxy box from the backend server are performed manually.

14. A non-transitory computer-readable medium storing instructions thereon which when executed by a computer processor controls the computer system to perform the steps of method according to claim 10.

* * * * *